(12) United States Patent
Milius et al.

(10) Patent No.: US 6,566,305 B1
(45) Date of Patent: May 20, 2003

(54) PHYTOSANITARY TREATMENT BY FOLIAR ABSORPTION USING A MODIFIED OIL

(75) Inventors: Alain Milius, Nice (FR); Christian Gauvrit, Dijon (FR); Thomas Muller, Ostfildern Allemagne (FR); Nathalie Okori, Lempaut (FR)

(73) Assignee: Societe d'Exploitation de Produits pour les Industries Chimiques SEPPIC, Paris Cedex (FR)

( * ) Notice: Subject to any disclaimer, the term of this patent is extended or adjusted under 35 U.S.C. 154(b) by 0 days.

(21) Appl. No.: 09/720,982

(22) PCT Filed: Jul. 1, 1999

(86) PCT No.: PCT/FR99/01583

§ 371 (c)(1),
(2), (4) Date: Apr. 5, 2001

(87) PCT Pub. No.: WO00/01233

PCT Pub. Date: Jan. 13, 2000

(30) Foreign Application Priority Data

Jul. 3, 1998 (FR) ............................................ 98 08521

(51) Int. Cl.$^7$ ................................................. A01N 3/02
(52) U.S. Cl. .................................................... 504/116.1
(58) Field of Search ....................................... 504/116.1

(56) References Cited

U.S. PATENT DOCUMENTS 4,557,751 A * 12/1985 Ronning et al. ............... 71/91

FOREIGN PATENT DOCUMENTS

| EP | 0 933 025 A1 | | 8/1999 |
|---|---|---|---|
| JP | 60-132904 | | 7/1985 |
| JP | 60132904 | * | 7/1985 |
| WO | WO 92/06596 | | 4/1992 |
| WO | 96/01047 | | 1/1996 |
| WO | WO 96/22109 | | 7/1996 |
| WO | 9800008 | * | 1/1998 |
| WO | 98/00008 | | 1/1998 |
| WO | 99/27780 | | 6/1999 |
| WO | 99/29170 | | 6/1999 |
| WO | 99/33340 | | 7/1999 |

* cited by examiner

*Primary Examiner*—Alton Pryor
(74) *Attorney, Agent, or Firm*—Young & Thompson

(57) ABSTRACT

The subject of the invention is a method of plant-protection treatment by leaf absorption, characterized in that it uses a composition comprising at least one plant-protection active ingredient and at least one modified oil, a composition comprising at least one plant-protection active ingredient, at least one modified vegetable oil and at least one unmodified vegetable oil as well as an alkoxylated vegetable oil containing x% of glycerol.

6 Claims, No Drawings

PHYTOSANITARY TREATMENT BY FOLIAR ABSORPTION USING A MODIFIED OIL

This Application is a 371 of PCT/FR99/01583 filed Jul. 1, 1999.

The subject of the invention is a method for plant-protection treatment by leaf absorption, using a combination between an active ingredient and a modified oil and a novel combination for using said method.

The use of oils is very widespread in the plant-protection domain; they are used either as formulation adjuvants, to increase the efficacy of the active substances, or as coformulants. Most of the oils used are of petroleum origin and are formulated with surfactants containing aromatic nuclei such as ethoxylated alkylphenols. However, surfactants containing an aromatic nucleus are not rapidly biodegradable and damage the ecosystems. For this reason, the use of rapeseed oil or of methyl esters of rapeseed oil is now growing; however, this oil is difficult to formulate, it is a less satisfactory solvent for the active ingredient than oils of petroleum origin and, since it does not possess intrinsic surfactant properties, it has to be used in combination with surfactants containing an aromatic nucleus. In the international patent application, published under the number WO 96/22109, ethoxylated fatty acid esters are described as self-emulsifiable compounds which can be used in formulations of plant-protection active ingredients such as ethephon or chlorpropham; however, nothing is written or suggested on the activity of the compositions resulting from this combination. However, the penetration of the plant-protection active ingredient into the plant occurs either at the level of the leaves, through leaf absorption, or at the level of the roots, through radicular absorption; it is known furthermore that leaf absorption of an active ingredient is often difficult; it is observed that after seventy-two hours, up to 95% of the active ingredient is still not absorbed by the plant. A period of rain following the treatment of a crop therefore risks inducing pollution of the site, while a period of sunshine can cause the degradation of the active ingredient. The work by C. Gauvrit and F. Cabanne [Pesticide Science, 37, 147–153 (1993)] has recently made it possible to demonstrate that the increase in the efficacy of herbicides in the presence of oils is attributed to a spreading of the droplets deposited at the surface of the leaves, and to a better leaf penetration of the herbicidal active ingredient. However, these effects, for the oils used up until now, only manifest themselves markedly on plants containing crystalline cuticular waxes, such as for example the Gramineae, whereas on the amorphous cuticular waxes of dicotyledons, the effects of these oils are more modest [C. Urvoy, M. Pollacsek and C. Gauvrit, Weed Research, 32, 375–383 (1992); I. Serre, F. Cabanne and C. Gauvrit, Medelingen van de Facultelt Landbouwwentenschappen Rijksuniversiteit Gent 58/3a, 795–802 (1993)]. Starting from the hypothesis that oils can increase the leaf penetration of the products by acting on the availability of the active substances at the surface of the leaf and on the mobility of the substances in the diffusion barrier which the plant cuticle constitutes [I. Serre, University of, Grenoble thesis (1996); I. Serre, F. Cabanne and C. Gauvrit, British Crop Protection Conference 7B-3, 807–812 (1996)], the applicant has thus sought to develop a method of plant-protection treatment by leaf absorption which allows, in a short time, a high level of absorption of the active ingredient by the plant while limiting the nuisances to the ecosystems, by the use of a composition which is sufficiently effective as solvent for the active ingredient and sufficiently stable over time to be marketable.

The subject of the invention is a method of plant-protection treatment by leaf absorption, characterized in that it uses a composition comprising at least one plant-protection active ingredient and at least one modified oil.

The expression modified oil denotes either alkoxylated or else and in particular ethoxylated and/or propoxylated oils, or alkoxylated alkyl esters of the oils and in particular ethoxylated and/or propoxylated methyl, ethyl, linear or branched propyl, or linear or branched butyl esters of said oils. According to a specific aspect of the present invention, the ethoxylated oils or the ethoxylated alkyl esters of vegetable oils each have an ethylene oxide number, called in the text which follows EO value, of between 1 and 50.

The modified oils used in the context of the present invention may be of mineral, plant or animal origin. Among the modified oils of mineral origin which may be used in the method as defined above, there are in particular the modified oils of petroleum origin; among the modified oils of animal origin which may be used in the method as defined above, there are in particular modified tallow oil; among the modified oils of plant origin which may be used in the method as defined above, there are, for example, modified sunflower, linseed, castor, soybean, corn, groundnut, copra, olive, palm, hydrogenated palm or rapeseed oils.

The expression at least one modified oil indicates that the composition used in the method which is the subject of the present invention may comprise either a single modified oil or a mixture of several modified oils; in the latter case, this may include a mixture of modified oils of the same origin or a mixture of modified oils of different origins.

The expression plant-protection treatment is understood to mean in the context of the present invention preferably a fungicidal, insecticidal or herbicidal treatment.

According to a specific variant of the method as defined above, the plant-protection composition used contains at least one modified vegetable oil, alone or in the form of a mixture with one or more modified oils of the same origin or of different origins.

According to another specific variant of the method as defined above, the plant-protection composition used contains, in addition, an unmodified vegetable oil or a mixture of unmodified vegetable oils. The expression unmodified vegetable oil is understood to mean vegetable oils or their alkyl esters, such as for example the methyl, ethyl, linear or branched propyl, or linear or branched butyl esters.

According to another aspect of the present invention, its subject is a composition comprising at least one plant-protection active ingredient, at least one modified vegetable oil and at least one unmodified oil.

The unmodified oil contained in the above composition is an oil of plant, animal or mineral origin. The expression unmodified oil is understood to mean oils or their alkyl esters, such as for example the methyl, ethyl, linear or branched propyl, or linear or branched butyl esters.

The subject of the invention is more particularly a composition as defined above in which the oil or the mixture of unmodified oils is of plant origin and is preferably chosen from sunflower, linseed, castor, soybean, corn, groundnut, copra, olive, palm, hydrogenated palm or rapeseed oils.

The expression modified vegetable oil denotes either alkoxylated vegetable oils and in particular ethoxylated and/or propoxylated vegetable oils, or alkoxylated alkyl esters of the oils and in particular ethoxylated and/or propoxylated methyl, ethyl, linear or branched propyl, or linear or branched butyl esters. According to a specific aspect of the present invention, the ethoxylated oils or the ethoxylated alkyl esters of vegetable oils each have an ethylene oxide number, called in the text which follows EO value, of between 1 and 50.

The subject of the invention is more particularly a composition as defined above which comprises at least one ethoxylated methyl ester of a vegetable oil having an EO value of between 1 and 4, more particularly of equal to 1 or 2 and at least one unmodified oil. According to a most specific aspect of the present invention, the composition comprises an ethoxylated methyl ester of a vegetable oil and the same vegetable oil which is unmodified. The ester of ethoxylated vegetable oil/unmodified vegetable oil weight ratio is in general between 1/50 and 50/1 and more particularly between 1/9 and 9/1.

The subject of the invention is also more particularly a composition comprising at least one plant-protection active ingredient, at least one ethoxylated vegetable oil having an EO value of between 10 and 40 and more particularly greater than or equal to 15 and less than or equal to 30, and at least one unmodified oil. According to a most specific aspect of the present invention, the composition as defined above comprises an ethoxylated vegetable oil, and the same vegetable oil which is unmodified. The ethoxylated vegetable oil/unmodified oil weight ratio is generally between 1/50 and 50/1 and more particularly between 1/9 and 9/1.

To improve its stability in the cold, the alkoxylated oil may be prepared by incorporating, before its alkoxylation, from 1 to 10% by weight of glycerol. This problem may also be solved by combining, in the same composition, an alkoxylated vegetable oil as defined above and an alkoxylated alkyl ester of vegetable oil, as defined above, and more particularly an ethoxylated and/or propoxylated methyl, ethyl, linear or branched propyl, or linear or branched butyl ester of a vegetable oil and, more particularly, by combining an ethoxylated vegetable oil having an EO value of between 10 and 40 and preferably greater than or equal to 15 and less than or equal to 30, with an ethoxylated methyl ester of a vegetable oil having an EO value of between 1 and 4, preferably equal to 1 or 2.

According to a final aspect of the present invention, its subject is a modified vegetable oil capable of being obtained by mixing, in the presence of a basic catalyst, from 1 to 10 parts of glycerol per 100 parts of an unmodified vegetable oil chosen from sunflower oil, linseed oil, castor oil, soybean oil, corn oil, groundnut oil, copra oil, olive oil, palm oil or hydrogenated palm oil, and then alkoxylating the resulting mixture; and more particularly a modified vegetable oil as defined above for which the average degree of ethoxylation is approximately greater than or equal to 10, preferably greater than or equal to 15, and less than or equal to 40, and preferably less than or equal to 30. The following examples illustrate the invention without, however, limiting it.

EXAMPLE 1

PREPARATION OF MODIFIED OILS

A) Preparation of Ethoxylated Methyl Esters of Rapeseed Oil

Starting with the methyl ester of rapeseed oil, by reacting for 45 minutes approximately at 180° C., with the quantity of ethylene oxide necessary for obtaining the desired molar ratio, at a pressure of 4.5 bar, in the presence of a basic catalyst, and then cooling and neutralizing the catalyst, the following ethoxylated methyl esters of rapeseed oils were prepared:

| COMPOUND | ETHOXYLATION VALUE |
|---|---|
| 1 | 0 |
| 2 | 1 |
| 3 | 2 |
| 4 | 3 |
| 5 | 4 |
| 6 | 6 |
| 7 | 8 |

B) Preparation of Ethoxylated Rapeseed Oils Containing 2% Glycerol

Using the ethoxylation method described in the preceding paragraph, in the presence of 2% by weight of glycerol, on rapeseed oil, the following ethoxylated rapeseed oils containing 2% of glycerol are obtained:

| COMPOUND | ETHOXYLATION VALUE |
|---|---|
| 8 | 15 |
| 9 | 20 |
| 10 | 25 |

C) Preparation of Ethoxylated Rapeseed Oils Containing x% of Glycerol

Using the ethoxylation method described in the preceding paragraph, on rapeseed oil in the presence of variable quantities of glycerol, the following ethoxylated rapeseed oils containing x% of glycerol are obtained:

| COMPOUND | ETHOXYLATION VALUE | % GLYCEROL |
|---|---|---|
| 11 | 20 | 1 |
| 12 | 20 | 2 |
| 13 | 20 | 5 |
| 14 | 20 | 10 |
| 15 | 0 | 2 |
| 16 | 3 | 2 |
| 17 | 6 | 2 |
| 18 | 10 | 2 |
| 19 | 20 | 2 |
| 20 | 30 | 2 |
| 21 | 40 | 2 |

D) Preparation of Ethoxylated Linseed Oils Containing 2% of Glycerol

Using the ethoxylation method described in paragraph A in the presence of 2% by weight of glycerol, on linseed oil, the following ethoxylated linseed oils containing 2% of glycerol are obtained:

| COMPOUND | ETHOXYLATION VALUE | % GLYCEROL |
|---|---|---|
| 22 | 0 | 2 |
| 23 | 10 | 2 |
| 24 | 20 | 2 |
| 25 | 30 | 2 |
| 26 | 40 | 2 |

E) Preparation of Ethoxylated Methyl Esters of Sunflower Oil

Using the ethoxylation method described in the preceding paragraph, on the methyl ester of sunflower oil, the following ethoxylated methyl esters of sunflower oil are obtained:

| COMPOUND | ETHOXYLATION VALUE |
|---|---|
| 27 | 2 |

F) Preparation of Ethoxylated Sunflower Oils Containing 4% of Glycerol

Using the ethoxylation method described in paragraph A in the presence of 4% by weight of glycerol, on sunflower oil, the following ethoxylated sunflower oils containing 4% of glycerol are obtained:

| COMPOUND | ETHOXYLATION VALUE | % GLYCEROL |
|---|---|---|
| 28 | 0 | 4 |
| 29 | 1 | 4 |
| 30 | 3 | 4 |
| 31 | 6 | 4 |
| 32 | 10 | 4 |
| 33 | 20 | 4 |
| 34 | 30 | 4 |
| 35 | 40 | 4 |

G) Preparation of Ethoxylated Corn Oils Containing 2% of Glycerol

Using the ethoxylation method described in paragraph A in the presence of 2% by weight of glycerol, on corn oil, the following ethoxylated corn oils containing 2% of glycerol are obtained:

| COMPOUND | ETHOXYLATION VALUE | % GLYCEROL |
|---|---|---|
| 36 | 0 | 2 |
| 37 | 10 | 2 |
| 38 | 20 | 2 |
| 39 | 30 | 2 |
| 40 | 40 | 2 |

EXAMPLE 2

PHYSICOCHEMICAL EVALUATION OF THE MODIFIED OILS

The solubilities in water and in an aqueous solution containing 10% by weight of sodium lauryl ether sulfate, the emulsifying power, the self-emulsifying power and the wetting power were evaluated according to conventional methods, for each of the modified oils prepared. The result is that compounds 2, 3, 8 to 13, 19 to 21, 24 to 27, 33 to 35 and 38 to 40 are more appropriate than the others for carrying out the method which is the subject of the present invention.

EXAMPLE 3

STUDY OF THE CAPACITY OF THE MODIFIED VEGETABLE OILS TO STIMULATE LEAF PENETRATION OF A PLANT-PROTECTION ACTIVE INGREDIENT

A) Phenmedipham Compositions

The penetration into barley (*Hordeum vulgare*) leaves, of phenmedipham, which [lacuna] a herbicide having a high melting point (greater than 100° C.) called 3-[(methoxycarbonyl)amino]phenyl(3-methylphenyl)-carbamate, alone or in combination with modified oils, was compared according to the following procedure: The carbon-14 labeled phenmedipham is dissolved (42 bq $\mu l^{-1}$), in the presence or in the absence of modified vegetable oils (about 10 nM), in acetone, a solvent which does not affect the cuticular waxes and which, by evaporating rapidly, does not interfere with the penetration process. Ten drops are applied to the adaxial surface of the first leaf. After 0, 4, 6, 24 or 72 hours, the product which has not penetrated is washed with 0.5 ml of acetone and the radioactivity measured by liquid scintillation. The radioactivity present in the treated leaf in the rest of the plant is determined in the carbon dioxide obtained after burning the tissue. The results, expressed as a percentage of the active ingredient which has penetrated into the leaf, are presented in the following table:

| COMPOSITION | LEAF PENETRATION AT: | | |
|---|---|---|---|
| | 06 HOURS | 24 HOURS | 72 HOURS |
| PHENMEDIPHAM ALONE | | | <10% |
| PHENMEDIPHAM + COMPOUND 36 | ~45% | ~80% | ~80% |
| PHENMEDIPHAM + COMPOUND 37 | ~40% | ~60% | ~70% |
| PHENMEDIPHAM + COMPOUND 38 | ~25% | ~50% | ~55% |
| PHENMEDIPHAM + COMPOUND 39 | ~20% | ~40% | ~55% |
| PHENMEDIPHAM + COMPOUND 40 | ~10% | ~30% | ~40% |
| PHENMEDIPHAM + COMPOUND 22 | ~75% | >80% | >80% |
| PHENMEDIPHAM + COMPOUND 23 | ~40% | ~70% | ~75% |
| PHENMEDIPHAM + COMPOUND 24 | ~20% | ~50% | ~55% |
| PHENMEDIPHAM + COMPOUND 25 | ~20% | ~50% | ~50% |
| PHENMEDIPHAM + COMPOUND 26 | ~10% | ~40% | ~35% |
| PHENMEDIPHAM + COMPOUND 15 | ~65% | ~80% | >90% |
| PHENMEDIPHAM + COMPOUND 16 | ~60% | ~75% | ~80% |
| PHENMEDIPHAM + COMPOUND 17 | ~55% | ~70% | ~80% |
| PHENMEDIPHAM + COMPOUND 18 | ~50% | ~70% | ~80% |
| PHENMEDIPHAM + COMPOUND 19 | ~25% | ~55% | ~70% |
| PHENMEDIPHAM + COMPOUND 20 | ~25% | ~55% | ~75% |
| PHENMEDIPHAM + COMPOUND 21 | ~15% | ~45% | ~65% |
| PHENMEDIPHAM + COMPOUND 28 | ~80% | ~75% | ~75% |
| PHENMEDIPHAM + COMPOUND 29 | ~80% | ~85% | ~90% |
| PHENMEDIPHAM + COMPOUND 30 | ~80% | ~85% | ~90% |
| PHENMEDIPHAM + COMPOUND 31 | ~60% | ~65% | ~60% |
| PHENMEDIPHAM + COMPOUND 32 | ~60% | ~75% | ~90% |
| PHENMEDIPHAM + COMPOUND 33 | ~35% | ~55% | ~60% |
| PHENMEDIPHAM + COMPOUND 34 | ~35% | ~60% | ~65% |
| PHENMEDIPHAM + COMPOUND 35 | ~30% | ~50% | ~60% |
| PHENMEDIPHAM + COMPOUND 11 | ~50% | ~75% | ~80% |

-continued

| COMPOSITION | LEAF PENETRATION AT: | | |
|---|---|---|---|
| | 06 HOURS | 24 HOURS | 72 HOURS |
| PHENMEDIPHAM + COMPOUND 12 | ~50% | ~75% | ~75% |
| PHENMEDIPHAM + COMPOUND 13 | ~50% | ~75% | ~70% |
| PHENMEDIPHAM + COMPOUND 14 | ~50% | ~75% | ~75% |
| PHENMEDIPHAM + COMPOUND 27 | >80% | ~85% | ~90% |
| PHENMEDIPHAM + COMPOUND 1 | ~95% | ~90% | ~90% |
| PHENMEDIPHAM + COMPOUND 2 | ~90% | ~90% | ~90% |
| PHENMEDIPHAM + COMPOUND 3 | ~85% | ~90% | ~90% |
| PHENMEDIPHAM + COMPOUND 4 | ~80% | ~85% | ~90% |
| PHENMEDIPHAM + COMPOUND 5 | ~80% | ~85% | ~90% |
| PHENMEDIPHAM + COMPOUND 6 | ~75% | ~75% | ~75% |
| PHENMEDIPHAM + COMPOUND 7 | ~65% | ~75% | ~80% |

B) 2,4-D Compositions

The penetration into barley (*Hordeum vulgare*) leaves, of 2,4-D or (2,4-dichlorophenoxy)acetic acid, which is a herbicide with a highly dissociated carboxylic acid function, alone or in combination with modified oils, was compared according to the procedure described in the preceding paragraph.

The following results are obtained:

| COMPOSITION | LEAF PENETRATION AT: | | |
|---|---|---|---|
| | 06 HOURS | 24 HOURS | 72 HOURS |
| 2,4-D ALONE | — | 10% | 15% |
| 2,4-D + COMPOUND 15 | — | >70% | >80% |
| 2,4-D + COMPOUND 16 | — | >70% | >80% |
| 2,4-D + COMPOUND 17 | — | >70% | >80% |
| 2,4-D + COMPOUND 18 | | >70% | >80% |
| 2,4-D + COMPOUND 19 | | >70% | >80% |
| 2,4-D + COMPOUND 20 | | >70% | >80% |
| 2,4-D + COMPOUND 21 | | >70% | >80% |

These results demonstrate the benefit of combining one or more modified oils with an active ingredient which is anionic and/or has a high melting point (>100° C.), for a plant-protection treatment by leaf absorption.

What is claimed is:

1. Method of plant-protection treatment by leaf absorption, which comprises applying to the leaves of plants to be protected a composition consisting essentially of a plant-protection active ingredient, and at least one modified oil selected from the group consisting of sunflower, linseed, soybean, corn, groundnut copra, olive, palm, hydrogenated palm and rape-seed oils.

2. Composition consisting essentially of a plant-protection active ingredient; at least one modified oil selected from the group consisting of sunflower, linseed, soybean, corn, groundnut, copra, olive, palm, hydrogenated palm and rape-seed oils; and at least one unmodified oil selected from the group consisting of sunflower, linseed, soybean, corn, groundnut, copra, olive, palm, hydrogenated palm and rape-seed oils.

3. Composition consisting essentially of a plant-protection active ingredient; at least one modified oil selected from the group consisting of sunflower, linseed, soybean, corn, groundnut, copra, olive, palm, hydrogenated palm and rape-seed oils; and at least one unmodified oil selected from the group consisting of sunflower, linseed, soybean, corn, groundnut, copra, olive, palm, hydrogenated palm and rape-seed oils, and wherein the modified vegetable oil or the mixture of modified vegetable oils is chosen from ethoxylated and/or propoxylated vegetable oils, or from ethoxylated and/or propoxylated methyl, ethyl, linear or branched propyl, or linear or branched butyl esters of vegetable oils.

4. Composition as defined in claim 3, in which the modified vegetable oil is an ethoxylated methyl ester having an EO value of between 1 and 4.

5. Composition consisting essentially of a plant-protection active ingredient; at least one modified oil selected from the group consisting of sunflower, linseed, soybean, corn, groundnut, copra, olive, palm, hydrogenated palm and rape-seed oils; and at least one unmodified oil selected from the group consisting of sunflower, linseed, soybean, corn, groundnut, copra, olive, palm, hydrogenated palm and rape-seed oils, and wherein the modified vegetable oil and the unmodified vegetable oil are derived from the same plant.

6. Composition consisting essentially of a plant-protection active ingredient; at least one modified oil selected from the group consisting of sunflower, linseed, soybean, corn, groundnut, copra, olive, palm, hydrogenated palm and rape-seed oils; and at least an ethoxylated methyl ester of a vegetable oil having an OE value of between 1 and 4 and ethoxylated vegetable oil having an EO value of 15 to 30.

* * * * *